United States Patent [19]
Klein et al.

[11] Patent Number: 5,767,098
[45] Date of Patent: Jun. 16, 1998

[54] ANTI-ACNE METHOD AND COMPOSITION

[75] Inventors: Robert W. Klein, Fort Washington; Albert M. Packman, Dresher, both of Pa.

[73] Assignee: Dermik Laboratories, Inc., Collegeville, Pa.

[21] Appl. No.: 776,005

[22] PCT Filed: Oct. 11, 1994

[86] PCT No.: PCT/US94/11502

§ 371 Date: Mar. 31, 1997

§ 102(e) Date: Mar. 31, 1997

[87] PCT Pub. No.: WO96/10998

PCT Pub. Date: Apr. 18, 1996

Related U.S. Application Data

[63] Continuation of Ser. No. 225,409, Apr. 8, 1994, Pat. No. 5,446,028, which is a continuation of Ser. No. 891,449, May 29, 1992, abandoned, and a continuation of Ser. No. 243,883, Sep. 13, 1988, abandoned, which is a continuation-in-part of Ser. No. 61,951, Jul. 27, 1987, abandoned, which is a continuation of Ser. No. 808,627, Dec. 12, 1985, abandoned.

[51] Int. Cl.$^6$ .................. A61K 31/71; A61K 31/075
[52] U.S. Cl. .................. 514/43; 514/714; 514/859
[58] Field of Search .................. 514/43, 714, 859

[56] References Cited

U.S. PATENT DOCUMENTS

| | | | |
|---|---|---|---|
| 2,699,054 | 1/1955 | Conover | 260/559 |
| 2,712,517 | 7/1955 | Gourevitch et al. | 195/114 |
| 2,798,053 | 7/1957 | Brown | 260/2.2 |
| 2,886,505 | 5/1959 | Singleton et al. | 204/213 |
| 3,005,023 | 10/1961 | Miller | 260/559 |
| 3,019,173 | 1/1962 | Arishima et al. | 195/80 |
| 3,301,899 | 1/1967 | Kaplan et al. | 260/559 |
| 3,475,407 | 10/1969 | Birkenmeyer | 260/210 |
| 3,509,127 | 4/1970 | Kagan et al. | 260/210 |
| 3,513,155 | 5/1970 | Birkenmeyer et al. | 260/210 |
| 3,535,422 | 10/1970 | Cox et al. | 424/164 |
| 3,544,551 | 12/1970 | Kagan et al. | 260/210 |
| 3,952,099 | 4/1976 | Smith | 424/227 |
| 3,969,516 | 7/1976 | Stoughton | 424/181 |
| 3,989,815 | 11/1976 | Rajadhyaksha | 424/60 |
| 3,989,816 | 11/1976 | Rajadhyaksha | 424/60 |
| 3,991,203 | 11/1976 | Rajadhyaksha | 424/274 |
| 4,056,611 | 11/1977 | Young | 424/62 |
| 4,122,170 | 10/1978 | Rajadhyaksha | 424/180 |
| 4,132,781 | 1/1979 | Stoughton | 424/181 |
| 4,316,893 | 2/1982 | Rajadhyaksha | 424/180 |
| 4,387,107 | 6/1983 | Klein et al. | 424/338 |
| 4,444,762 | 4/1984 | Rajadhyaksha | 424/180 |
| 4,497,794 | 2/1985 | Klein et al. | 424/81 |
| 4,505,896 | 3/1985 | Bernstein | 424/164 |
| 4,671,956 | 6/1987 | Bouillon et al. | 424/59 |

FOREIGN PATENT DOCUMENTS

| | | |
|---|---|---|
| 0 027 286 | 4/1981 | European Pat. Off. |
| 1594314 | 7/1981 | United Kingdom. |

OTHER PUBLICATIONS

Tucker et al., Comparison of Topical Clindamycin Phosphate, Benzoyl Peroxide, and a Combination of the Two for the Treatment of Acne Vulgaris, British Journal of Dermatology, vol. 110, pp. 487–492 (1984).

Windholz (ed.) et al., Lincomycin, The Merck Index, 10th Ed., No. 5328 (1983).

*Primary Examiner*—Phyllis G. Spivack
*Attorney, Agent, or Firm*—Ross J. Oehler

[57] ABSTRACT

Compositions for treating acne that contain a peroxide and an antibiotic selected from the lincomycin family are disclosed. In particular, compositions containing benzoyl peroxide and clindamycin are disclosed along with methods of treating acne using these compositions.

20 Claims, No Drawings

5,767,098

ANTI-ACNE METHOD AND COMPOSITION

CROSS REFERENCE TO RELATED APPLICATIONS

This application is a continuation of application Ser. No. 225,409 filed Apr. 8, 1994, now issued as U.S. Pat. No. 5,446,028, which is a continuation of application Ser. No. 07/891,449 filed on May 29, 1992, abandoned and a continuation of Ser. No. 07/243,883, filed Sep. 13, 1988, abandoned, which is a continuation-in-part of Ser. No. 061,951, filed Jul. 27, 1987, abandoned, which is a continuation of Ser. No. 808,627, filed Dec. 12, 1985, abandoned.

FIELD OF THE INVENTION

This invention relates to a method and pharmaceutical composition useful for the topical treatment of acne.

Acne is a common inflammatory disease which is very common at puberty and which occurs in skin areas where sebaceous glands are largest, most numerous, and most active. In its milder forms, acne is a superficial disorder which is evidenced by slight, spotty irritations, and which can be treated satisfactorily by ordinary skin hygiene. However, pilosebaceous follicles occurs and results in the formation of pustules, infected cysts and, in extreme cases, canalizing inflamed and infected sacs, which may become extensive and leave permanent, disfiguring scars.

Therapeutic methods for treating acne include the systemic and topical administration of anti-acne agents such as antibiotics or derivatives of Vitamin A acid. In all but the severest of cases, systemic treatment of acne is not desirable because of side effects. However, systemic methods have been extensively used to treat acne because there has not been available a topical formulation which possess the level of therapeutic effectiveness desirable to relieve the unsightly symptoms of the acne disease condition.

One aspect of the present invention relates to an improved topical anti-acne composition.

REPORTED DEVELOPMENTS

Topical anti-acne preparations include, for example, sulfur, resorcinol, salicylic acid, benzoyl peroxide, and/or antibiotics. Exemplary antibiotics incorporated in compositions are disclosed in U.S. Pat. No. 3,969,516 (lincomycin family); BR Publication No. 1,594,314 (erythromycin); and U.S. Pat. No. 3,952,099 (tetracycline). Compositions containing a peroxide are reported in U.S. Pat. Nos. 3,535,422; 4,056,611; 4,387,107, and British Publication No. 1,594,314 and U.S. Pat. No. 4,497,794. Antibiotic-containing compositions which also include anti-inflammatory steroids are disclosed in U.S. Pat. No. 4,132,781.

Attempts to improve the effectiveness of topical antibiotic compositions for use in the treatment of acne have taken a number of approaches. One approach is reported in U.S. Pat. Nos. 3,989,815; 3,989,816; 3,991,203; 4,122,170; 4,316,893; 4,444,762; and EP 27,286, which disclose skin-penetrating vehicle compositions that reportedly increase the transdermal absorption of any physiologically active substance, including antibiotics. However, not all penetrating agents in combination with antibiotics are effective for the treatment of acne. For example, the aforesaid '781 patent discloses that the use of a skin-penetrating vehicle results in an effective anti-acne composition with erythromycin, but not with tetracycline.

A further approach relates to the use of a composition which utilized two different active agents, such as erythromycin, Vitamin A acid or benzoyl peroxide. Compositions including mixtures of a peroxide and erythromycin are reported in British Publication No. 1,594,314 and U.S. Pat. No. 4,497,794.

The reported topical anti-acne methods and compositions exhibit the disadvantages of limited effectiveness and frequent excessive adverse skin reactions.

SUMMARY OF THE INVENTION

This invention relates to a method for the treatment of acne comprising the topical administration, to a patient afflicted therewith, of a topically effective amount of a peroxide and an antibiotic from the lincomycin or tetracycline families.

As noted above, the prior art discloses compositions which include separately benzoyl peroxide or an antibiotic of the lincomycin or tetracycline family. Another aspect of the present invention relates to a composition which is effective in the treatment of acne, and which includes, as essential ingredients, a peroxide and an antibiotic from the lincomycin or tetracycline families or a pharmaceutically acceptable salt or ester thereof.

Another aspect of this invention is the provision of a stable anti-acne composition by adjusting the pH of the composition to an effective stabilizing pH and/or by incorporating an effective stabilizing amount of docusate salts, such as dioctyl sodium sulfosuccinate.

An advantage of the present invention relates to the surprising speedy onset of effectiveness.

These and other aspects of the present invention are described in more detail below.

DETAILED DESCRIPTION

The term "antibiotic of the lincomycin family" is used herein to refer to a class of antibiotic substances originally recovered from *streptomyces lincolnensis*.

Exemplary antibiotics include lincomycin and clindamycin and their pharmaceutically acceptable salts and esters such as their hydrochlorides and phosphates. Lincomycin is a derivative of the amino acid trans-L-4-α-propyl-hygrinic acid coupled to a derivative of an octose substituted by a methylmercaptyl group. Clindamycin is the 7-deoxy, 7-chloro derivative of lincomycin, and is otherwise known as methyl 7-chloro-6,7,8,trideoxy-6-[[(1-methyl-4-propyl-2-pyrrolidinyl) carbonyl]amino]-1-thio-L-threo-α-D-galacto-octopyranoside. The lincomycin antibiotics are described in U.S. Pat. Nos. 3,475,407; 3,509,127; 3,544,551 and 3,513,155.

The term "antibiotic of the tetracycline family" is used herein to refer to a class of antibiotic substances originally recovered from *streptomyces aureofaciens*. Exemplary tetracyclines include chlortetracycline, oxytetracycline, tetracycline, demeclocycline, rolitetracycline, methacycline and doxycycline and their pharmaceutically acceptable salts such as acid addition salts, for example, their hydrochloride salts. Tetracycline, otherwise known as 4-(Dimethylamino)-1,4,4a,5,5a,6,11,12a-octahydro-3,6,12,12a-pentahydroxy-6-methyl-1,-11dioxo-2-naphthacene-carboxamide, is described in U.S. Pat. Nos. 2,699,054; 2,712,517; 2,886,505; 3,005,023; 3,019,173; and 3,301,899. A review of tetracycline is published in "The Technology of the Tetracyclines," Vol. I. R. C. Evans, Ed. (Quadrangle Press, N.Y., 1968).

The term "peroxide" means an organic compound containing an oxygen-oxygen bond capable of cleaving and forming oxygen free-radicals. The peroxides include peroxyacids of carboxylic acids, peroxyesters of carboxylic acids and the dimeric product of carboxylic peroxyacids. Exemplary peroxides include t-butyl peroxyesters of straight and branched chain aliphatic carboxylic acids, and dimeric peroxides such as lauroyl peroxide and benzoyl peroxide. A preferred peroxide for use in the present invention is benzoyl peroxide, and the most preferred is micronized benzoyl peroxide.

The method of the present invention comprises the administration of an antibiotic of the lincomycin or tetracycline families to the skin of a patient suffering from acne either simultaneously with or shortly prior to or after the application of the peroxide. Accordingly, the two ingredients may be applied to the skin as a mixture or they may separately be applied to the skin. In the latter practice the antibiotic is applied first to the skin and immediately or shortly thereafter the peroxide in applied. Or, the order of application is reversed.

The composition of the present invention includes as essential ingredients benzoyl peroxide and an antibiotic from the lincomycin or tetracycline families, a preferred form of the composition comprising microsized benzoyl peroxide and clindamycin or tetracycline or a pharmaceutically acceptable salt or ester thereof. The most preferred composition includes clindamycin.

The peroxide is present in the composition in an amount of about 1% to about 30 wt. %, and preferably about 2.5% to 15 wt. % based on the total weight of the composition. A most preferred amount of peroxide is about 5 to about 10 wt. %. The preferred peroxide should be of high purity. An exemplary material includes peroxide in an amount which is not less than about 98% of the stated concentration on the labeled raw material and in the form of finely divided crystalline particles, preferably, micronized particles having a mean average particle size of less than about 35 microns.

The antibiotic is present in the composition in an amount of about 0.01 to about 5 weight percent of the total composition, and preferably from about 0.1 to about 3 weight percent.

A preferred composition is in the form of an aqueous gel, and the most preferred composition is an aqueous alcoholic gel. However, liquid suspensions and emulsions, as well as creams, ointments and powders are acceptable.

The gelling agent used in the preferred composition of this invention may be selected both as to type and quantity to give products of various viscosities. A variety of gelling agents may be used for the present purposes. Preferred gelling agents are pure micro-crystalline cellulose, colloidal magnesium silicate, hydroxypropyl methyl cellulose and the so-called hydroxylated vinylic polymers, particularly, those disclosed in U.S. Pat. No. 2,798,053. Those hydroxylated vinylic polymers of special interest herein can be described generally as interpolymers prepared from a monomeric mixture comprising a mono-olefinic acrylic acid and about 0.1% to about 10% by weight of the other monomers in the monomeric mixture of polyether of an oligosaccharide having hydroxyl groups which are etherified with allyl groups, said oligosaccharide containing at least two allyl groups per oligosaccharide molecule. Commercially available interpolymers of this type are marketed under the trademark Carbopols®. These are described as being polymers of acrylic acid cross-linked with about 1% of a polyalkyl ether of sucrose having an average of about 5.8 alkyl groups for each sucrose molecule. These polymers have molecular weight in the order of magnitude of 1,000,000. Such polymers are available from the B. F. Goodrich Chemical Company and are sold under such trademarks as Carbopol® 940 and Carbopol® 941. Closely related copolymers, such as Carbopol® 1342 are also acceptable.

The amount of gelling agent included in the present preferred gel composition can range from about 0.1 to about 15% by weight, and preferably from about 0.5 to about 3% by weight, based on the total weight of the composition.

The composition of the present invention may include a surface active agent or dispersing agent to disperse uniformly the active ingredients. A preferred composition includes a second surface active agent. Such agents include the esters of polyols and sugars, the products of the condensation of ethylene oxide with fatty acids, fatty alcohols, long-chain alkylphenols, long-chain mercaptans, long chain amides, polyethers of polyhydroxylated fatty alcohols and alkylpolyglycol ethers which are included in an amount of from about 2% to about 6% by weight.

Another preferred embodiment of the composition of the present invention has a pH which is effective in stabilizing the antibiotic and peroxide ingredients over time. The effective stabilizing pH is about 4.6 to about 5.7, and the preferred stabilizing pH is about 5.2 to about 5.5. The most preferred pH is about 5.3.

A further preferred composition of the present invention includes a stabilizing agent which acts as an effective barrier to the possible degrative interaction of the peroxide and the antibiotic. The preferred stabilizing agent is dioctyl sodium sulfosuccinate, for example, an amount of about 0.1 to about 6% by weight, and preferably about 0.5% to about 3% by weight.

One type of preparation may comprise a two-component system, wherein one component comprises the antibiotic in stable form and the other component comprises the peroxide component. Another type of preparation comprises a composition in which the two active ingredients are stabilized as described hereinabove and may coexist relatively unchanged at temperatures conventionally employed for the storage of clindamycin or tetracycline solutions. Conventional pharmaceutical processes may be used in making up these common forms of medicinal, topical compositions.

As mentioned above, a basic type of topical preparation comprises a mixture of powdered peroxide and antibiotic with an inert diluent. Such a preparation should be sparingly applied to the skin.

The following examples are illustrative of the present invention.

EXAMPLE 1

The following ingredients are mixed together to form a powder which may be dusted on the affected skin area, from one to four times a day.

|  | W/W Percent |
| --- | --- |
| benzoyl peroxide | 1–35 |
| calcium phosphate | 63–98.5 |
| clindamycin hydrochloride | 0.1–5 |

EXAMPLE 2

A liquid suspension of the present invention may be prepared by combining the following ingredients.

| | W/W Percent |
|---|---|
| water | Q.S.-100 |
| clindamycin hydrochloride | 0.5-5 |
| benzoyl peroxide | 1-30 |

Other preparations which are representative of the present invention include the following examples.

EXAMPLE 3

A lotion manufactured in a two component system may be prepared as follows. The following ingredients are mixed in a first container.

| | W/W Percent |
|---|---|
| stearyl alcohol (and) Ceteareth-20 | 5.5 |
| cetyl alcohol | 0.75 |
| C12-15 alcohols benzoate | 5 |
| butylated hydroxyanisole | 0.1 |
| PEG-100 stearate | 0.25 |
| water, deionized or distilled | 70.3 |
| propylene glycol | 3.0 |
| benzoyl peroxide | 5.0 |
| acetone | 10.0 |
| dioctyl sodium sulfosuccinate | 0.1 |

A second container includes a solution of clindamycin hydrochloride (1% w/w of the total weight of the total composition) in an appropriate solvent, preferably water or ethanol. The amount of solvent used comprises an amount which dissolves about 2 grams of clindamycin HCl in about 3 cc of solvent.

Both containers may be put in a single marketable package with the instructions that the contents of the two containers be thoroughly mixed prior to the composition's application to the skin. For each 3 cc of solution in the second container, the first container contains about 20 grams of composition. An alternate method comprises the stepwise application of the composition in the first container and the clindamycin solution in the second container so that the two-part composition is mixed on the skin.

EXAMPLE 4

A cream is manufactured as follows:
The following ingredients are mixed in a first container:

| | W/W Percent |
|---|---|
| stearyl alcohol (and) Ceteareth-20 | 11 |
| cetyl-stearyl alcohol | 1.25 |
| C12-15 alcohol benzoate | 5 |
| butylated hydroxyanisole | 0.01 |
| PEG-100 stearate | 0.85 |
| water, deionized or distilled | 64 |
| propylene glycol | 3 |
| benzoyl peroxide | 5 |
| acetone | 10 |
| dioctyl sodium sulfosuccinate | 0.1 |

A second container includes a solution of clindamycin hydrochloride (2% w/w of the contents of the first container) in an amount of an appropriate solvent, preferably water or ethanol, such that 3 cc of the solution is prepared for each 20 grams of the composition in the first container.

EXAMPLE 5

A gel according to the present invention is prepared by combining the following ingredients in the first container.

| | W/W Percent |
|---|---|
| water, deionized or distilled | 54.65 |
| Veegum ® (R. T. Vanderbuilt Co.) | 1.5 |
| carboxy vinyl polymer (acid) | 1 |
| dioctyl sodium sulfosuccinate | 1 |
| diisopropanolamine | 0.75 |
| ethyl alcohol, 200° | 35.1 |
| benzoyl peroxide (micronized) | 5 |

Clindamycin phosphate (3% w/w of the total gel weight) is included in a second container.

EXAMPLE 6

A two-part suspension is prepared from the following ingredients.

| | W/W Percent |
|---|---|
| First Container | |
| water, deionized or distilled | 66.97 |
| Veegum ® (R. T. Vanderbuilt Co.) | 1.50 |
| polyacrylic acid | 0.25 |
| dioctyl sodium sulfosuccinate | 1 |
| diisopropanolamine | 0.18 |
| ethyl alcohol, 200° | 25 |
| butylated hydroxyanisole | 0.1 |
| benzoyl peroxide (micronized) | 5 |
| Second Container | |
| clindamycin hydrochloride | 2% W/W based on the total composition |

EXAMPLE 7

Lincomycin is substituted for clindamycin in the compositions of Examples 3 to 6.

EXAMPLE 8

In the composition of the above examples t-butyl peroctoate is substituted for benzoyl peroxide.

EXAMPLE 9

Tetracycline is substituted for clindamycin in the compositions of Examples 3 to 6.

EXAMPLE 10

Fifteen mg of Carbomer (15 mg) is added to distilled water (495 mg) while stirring. Stirring is continued for about 45 minutes. A solution of sodium hydroxide (4.09 mg) in distilled water (4.9 ml) is added and stirring continued for 10 minutes. Ethyl alcohol (150 ml) and methyl salicylate (1 mg) are added to the stirred solution, followed by wet pack micronized benzoyl peroxide (50% benzoyl peroxide—50% water) (210 mg), and distilled water (80 ml). The resulting mixture is stirred until a smooth gel is obtained.

A 20 g sample of the gel is mixed with a solution of clindamycin hydrochloride (800 mg) in distilled water (3 ml) affording a gel containing about 34.4. mg of clindamycin hydrochloride per gram of gel.

EXAMPLE 11

The following gel formulation including tetracycline is prepared according to the procedure described in Example 10.

|  | W/W Percent |
| --- | --- |
| benzoyl peroxide (microsized) | 5.46 |
| tetracycline | 2 |
| ethyl alcohol | 20 |
| PEG-8 caprate | 6 |
| colloidal magnesium aluminum silicate | 2.5 |
| hydroxyethylmethylcellulose | 0.75 |
| citric acid | 0.05 |
| dioctyl sodium sulfosuccinate | 0.05 |
| water | Q.S. |

The resultant product has good stability and is effective for use in the treatment of acne.

EXAMPLE 12

An aerosol spray according to the present invention may be prepared as follows.

The following ingredients, in amounts within the below indicated ranges, are blended together and the resulting mixture charged into one chamber of a dual chamber aerosol container.

|  | W/W Percent |
| --- | --- |
| benzoyl peroxide | 1–20 |
| calcium phosphate | 65–97 |
| calcium stearate | 1–10 |
| PPG-15 stearyl ether | 0.5–5 |

Clindamycin phosphate (0.1–5wt %) is charged into the second chamber of the container and the container is pressurized with aerosol propellant.

Comparative studies have shown unexpectedly that pH is a significant factor in determining the stability of the composition of the present invention. The active ingredients included in the compositions having a pH within the range described above are physically and chemically more stable than the ingredients included in compositions having a pH outside the defined range. This work is discussed in more detail below.

EXAMPLE 13

Aqueous gel compositions of varying pH are prepared according to the following formulation:

|  | W/W Percent |
| --- | --- |
| benzoyl peroxide | 5 |
| clindamycin phosphate | 1 |
| carbomer ® 940 | 1 |
| sodium hydroxide | to desired pH |
| water | QS |

Applicant has found that when compositions having different pH are subjected to accelerated decomposition conditions of 50° C., compositions having a pH below about 4.6 exhibit an unacceptable odor and evidence degradation of the peroxide. Similarly, compositions having a pH above about 5.7 show signs of clindamycin degradation. However, after 30 days, the composition having an initial pH of about 5.3 shows excellent stability. Neither peroxide nor clindamycin appear to degrade as measured by HPLC. The 30-day aged composition shows no evidence of peroxide decomposition and 90% of the clindamycin is retained in the composition.

The composition of the present invention may be applied to the afflicted skin of an acne sufferer for a period of time on a regular basis such that the acne condition is brought under control. A preferred regimen of treatment comprises the application of the composition from about one to about four times a day.

We claim:

1. A composition for the topical treatment of acne consisting essentially of a peroxide and antibiotic of the lincomycin family.

2. The composition according to claim 1, wherein the peroxide comprises benzoyl peroxide, and the antibiotic comprises clindamycin or a pharmaceutically acceptable salt or ester thereof.

3. The composition according to claim 2, having a pH of about 4.6 to about 5.7.

4. The composition according to claim 2 comprising about 1 to about 30 weight percent benzoyl peroxide and about 0.01 to about 5 weight percent clindamycin or a pharmaceutically acceptable salt or ester thereof.

5. The composition according to claim 1, wherein said composition is in the form of a gel, liquid suspension, emulsion cream, ointment or powder.

6. A method for treating acne comprising topical administration to a patient afflicted with acne of an effective amount of the composition according to claim 1.

7. A composition for the topical treatment of acne consisting essentially of a peroxide, an antibiotic of the lincomycin family and at least one surfactant.

8. The composition according to claim 7, wherein said composition is in the form of a gel, liquid suspension, emulsion, cream, ointment or powder.

9. The composition according to claim 7, wherein the peroxide comprises benzoyl peroxide, and the antibiotic comprises clindamycin or a pharmaceutically acceptable salt or ester thereof.

10. The composition according to claim 9 comprising about 1 to about 30 weight percent benzoyl peroxide and about 0.01 to about 5 weight percent clindamycin or a pharmaceutically acceptable salt or ester thereof.

11. The composition according to claim 7 having a pH of about 4.6 to about 5.7.

12. A method for treating acne comprising topical administration to a patient afflicted with acne of an effective amount of the composition according to claim 7.

13. A composition for the topical treatment of acne consisting essentially of a peroxide, an antibiotic of the lincomycin family and at least one inert diluent.

14. The composition according to claim 13, wherein said composition is in the form of a gel, liquid suspension, emulsion, cream, ointment or powder.

15. The composition according to claim 13, wherein the peroxide comprises benzoyl peroxide, and the antibiotic comprises clindamycin or a pharmaceutically acceptable salt or ester thereof.

16. The composition according to claim 15 comprising about 1 to about 30 weight percent benzoyl peroxide and about 0.01 to about 5 weight percent clindamycin or a pharmaceutically acceptable salt or ester thereof.

17. The composition according to claim 13 having a pH of about 4.6 to about 5.7.

18. A method for treating acne comprising topical administration to a patient afflicted with acne of an effective amount of the composition according to claim 13.

19. A composition for the topical treatment of acne comprising a peroxide and an antibiotic of the lincomycin family, wherein said composition is free of a sun filter.

20. A composition for the topical treatment of acne comprising a peroxide and an antibiotic of the lincomycin family without any other acne treatment agent.

* * * * *

UNITED STATES PATENT AND TRADEMARK OFFICE
CERTIFICATE OF CORRECTION

PATENT NO. : 5,767,098
DATED : June 16, 1998
INVENTOR(S) : Robert Klein & Albert M. Packman It is certified that error appears in the above-identified patent and that said Letters Patent is hereby corrected as shown below:

On the title page , please insert the following :

--[*]   Notice:   The term of this patent shall not extend beyond the expiration date of Pat. No. 5,446,028 --.

[45]   Date of Patent:   --*--Jun. 16, 1998 column 3, line 24, correct "microsized" to read --micronized--

Signed and Sealed this

Twenty-fifth Day of May, 1999

Attest:

Q. TODD DICKINSON

Attesting Officer

Acting Commissioner of Patents and Trademarks